(12) United States Patent
Don Michael

(10) Patent No.: US 9,855,127 B2
(45) Date of Patent: Jan. 2, 2018

(54) APPARATUS FOR PERFORMING A MEDICAL PROCEDURE IN THE CIRCULATORY SYSTEM

(71) Applicants: Don Michael International, LLC, Bakersfield, CA (US); Sharmini Don Michael, Bakersfield, CA (US)

(72) Inventor: T. Anthony Don Michael, Bakersfield, CA (US)

(73) Assignee: DON MICHAEL INTERNATIONAL, LLC, Bakersfield, CA (US)

( * ) Notice: Subject to any disclaimer, the term of this patent is extended or adjusted under 35 U.S.C. 154(b) by 113 days.

(21) Appl. No.: 15/143,898

(22) Filed: May 2, 2016

(65) Prior Publication Data
US 2017/0231744 A1    Aug. 17, 2017

Related U.S. Application Data

(60) Provisional application No. 62/303,279, filed on Mar. 3, 2016, provisional application No. 62/295,754, filed on Feb. 16, 2016.

(51) Int. Cl.
*A61F 2/24* (2006.01)
*A61F 2/01* (2006.01)

(52) U.S. Cl.
CPC ............ *A61F 2/013* (2013.01); *A61F 2/2427* (2013.01); *A61F 2002/018* (2013.01)

(58) Field of Classification Search
CPC .......... A61F 2/013; A61F 2/2427; A61F 2/00; A61F 2/01; A61F 2/2436; A61F 2002/018; A61F 2002/011; A61F 2002/016; A61F 2002/015; A61F 9/022
USPC .......................................... 606/114, 127, 200
See application file for complete search history.

(56) References Cited

U.S. PATENT DOCUMENTS

| | | | |
|---|---|---|---|
| 2009/0062840 A1* | 3/2009 | Angel | A61F 2/013 606/200 |
| 2010/0185179 A1* | 7/2010 | Chan | A61B 17/3478 604/508 |
| 2013/0289716 A1* | 10/2013 | Don Michael | A61F 2/013 623/2.11 |

* cited by examiner

*Primary Examiner* — Diane Yabut
*Assistant Examiner* — Erich Herbermann
(74) *Attorney, Agent, or Firm* — Browdy and Neimark, P.L.L.C.

(57) ABSTRACT

Apparatus for carrying out a medical procedure at a site in a patient's blood circulatory system, including a device to be implanted in the circulatory system, a sheath surrounding device and having a first diameter; a hollow tube having a second diameter and having a pressure transducer at its proximal end, and a filter that is collapsible into the sheath and is expandable out of the sheath for blocking debris and passing blood in the circulatory system.

4 Claims, 3 Drawing Sheets

APPARATUS FOR PERFORMING A MEDICAL PROCEDURE IN THE CIRCULATORY SYSTEM

BACKGROUND OF THE INVENTION

The present invention relates to an apparatus for aiding medical treatments in the blood circulation system of a patient, and in particular for minimizing unintended injury during the treatment, while preventing the circulation of embolic debris, or blood clots, resulting from such treatments. The invention is primarily, but not exclusively, concerned with providing protection in connection with procedures like those for implanting a prosthetic heart valve. The invention utilizes some components disclosed in co-pending Application No. PCT/US2012/61038, the disclosure of which is incorporated herein by reference.

There are known procedures, known as transcatheter aortic valve implantation (TAVI), in which a prosthetic heart valve is implanted at the site of a defective native valve, or of a previously implanted defective prosthetic valve. In these procedures, the new prosthetic valve and its guiding structure are introduced by a transcutaneous catheterization technique. For example, the valve and delivery components will be introduced through an incision in the groin or arm and along a blood vessel path to the desired location.

Such a procedure is disclosed, for example, in U.S. Pat. No. 7,585,321, which issued to Alan Cribier on Sep. 8, 2009, the entire disclosure of which is incorporated herein by reference. Such valves and their associated guiding devices are marketed by Medtronic and by Edwards Lifesciences, one example of the Edwards valves being marketed under the trade name Sapien.

Although such prosthetic valves have been used successfully to provide a replacement for stenotic native heart valves or defective prosthetic valves, it is difficult with known implantation procedures to guide the prosthetic valve to its intended location with sufficient accuracy to avoid traumatizing body tissue around the implantation site.

BRIEF SUMMARY OF INVENTION

The present invention provides an apparatus and procedure that guide a medical device to an implantation site more accurately.

To this end, apparatus according to the invention for carrying out a medical procedure at a site in a patient's blood circulatory system, comprises:
  a first assembly having an outer diameter and including a device to be implanted in the circulatory system;
  a tubular sheath surrounding the first assembly and having a first diameter;
  a hollow tube having a second diameter, distal and proximal ends, and an axial length between the distal and proximal ends, the hollow tube being open at both ends;
  a pressure transducer, or sensor, disposed at the proximal end of the hollow tube for detecting the pressure in the tube; and
  a filter that is collapsible into the sheath and expandable upon being deployed out of the sheath for blocking debris and passing blood in the circulatory system, at the site of the medical procedure, the filter having, when deployed, a radially expanded generally conical or frustoconical form with a large diameter end, a small diameter end opposite to the large diameter end, and a side surface extending between the large diameter end and the small diameter end,
  the filter:
  comprising a flexible filter material covering the side surface and having pores dimensioned to prevent the passage of debris therethrough while allowing the passage of blood, and
  having a first opening at the large diameter end, a second opening at the small diameter end, and a third opening in the flexible filter material at the side surface, each opening having a respective diameter,
wherein:
  the diameter of the second opening is substantially equal to the first diameter such that the second opening forms a seal with the sheath when the sheath extends into the filter through the second opening;
  the hollow tube is insertable, via the distal end, into the filter through the third opening; and
  the diameter of the third opening is substantially equal to the second diameter.

According to preferred embodiments of the invention, the hollow tube is controllable to displace the distal end in directions transverse to the axial length of the hollow tube, the hollow tube is a steerable catheter, the first assembly is a transaortic valve implantation assembly and the device to be implanted in the circulatory system includes a prosthetic valve.

A valve implantation procedure according to the present invention may include the following basic steps:
  the sheath with the retracted filter is introduced into the aorta toward the existing aortic valve and the filter is deployed out of the sheath and allowed to expand radially with the large diameter end facing the existing aortic valve, so that the filter obturates the aorta, preferably upstream of the coronary arteries;
  the hollow tube is introduced through the third opening to bring its distal end into the region enclosed by the expanded filter, thus blocking the third opening;
  the tubular sheath is introduced into the aorta and brought to a position in which its distal end is in contact with the first opening of the filter in a manner to assure that debris produced during valve implantation will flow into the tubular sheath and will thus be prevented from flowing into blood vessels communicating with the aorta;.
  then the distal end of the hollow tube will be displaced across the aorta, as by manipulating the proximal end of the hollow tube or by operating a known steering mechanism associated with the hollow tube, while monitoring the pressure of blood expelled through the existing aortic valve with the aid of the pressure transducer, to bring the distal end of the hollow tube to a desired location where the systolic blood pressure has a maximum value;
  then the valve implantation assembly is guided, as with the aid of fluoroscopic observation, to cause the prosthetic valve to be advanced alongside the distal end of the hollow tube, when the hollow tube is at the desired location, into the desired implantation position, aligned with the existing aortic valve, and the prosthetic valve is deployed into its desired implanted state; and
  finally, after a period of time to complete removal of any debris produced during the implantation procedure, all components of the apparatus are removed from the patient's body.

By introducing the prosthetic valve at a location corresponding to maximum blood pressure, trauma to the aortic wall, which could generate clots and other debris, is prevented, or at least minimized.

According to the invention, there may be provided, together with the filter and blocking device, a stent or stent graft that is preliminarily deployed against the inner wall of the blood vessel, e.g., the aorta, to prevent trauma during introduction of the filter.

The components of embodiments of the invention may be conveyed to the treatment site along various blood vessel paths and may be introduced via respectively different paths. For example, if the components are to be positioned in, or pass through, the aorta, one component can be introduced through an incision in a groin and the associated femoral artery, and another component can be introduced through an incision in an arm and the associated subclavian artery. Other introduction locations can also be used.

DETAILED DESCRIPTION OF THE INVENTION

Figure 1:
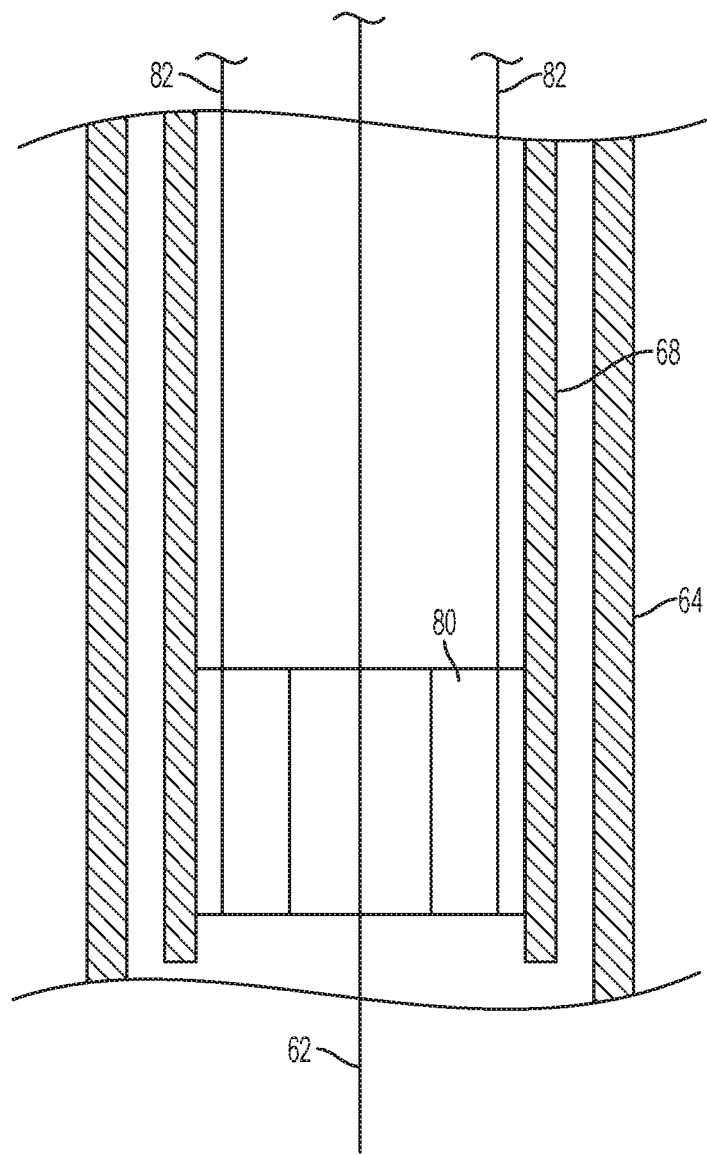
FIG. 1 is a cross-sectional view relating to a preferred embodiment of the invention.
Figure 2:
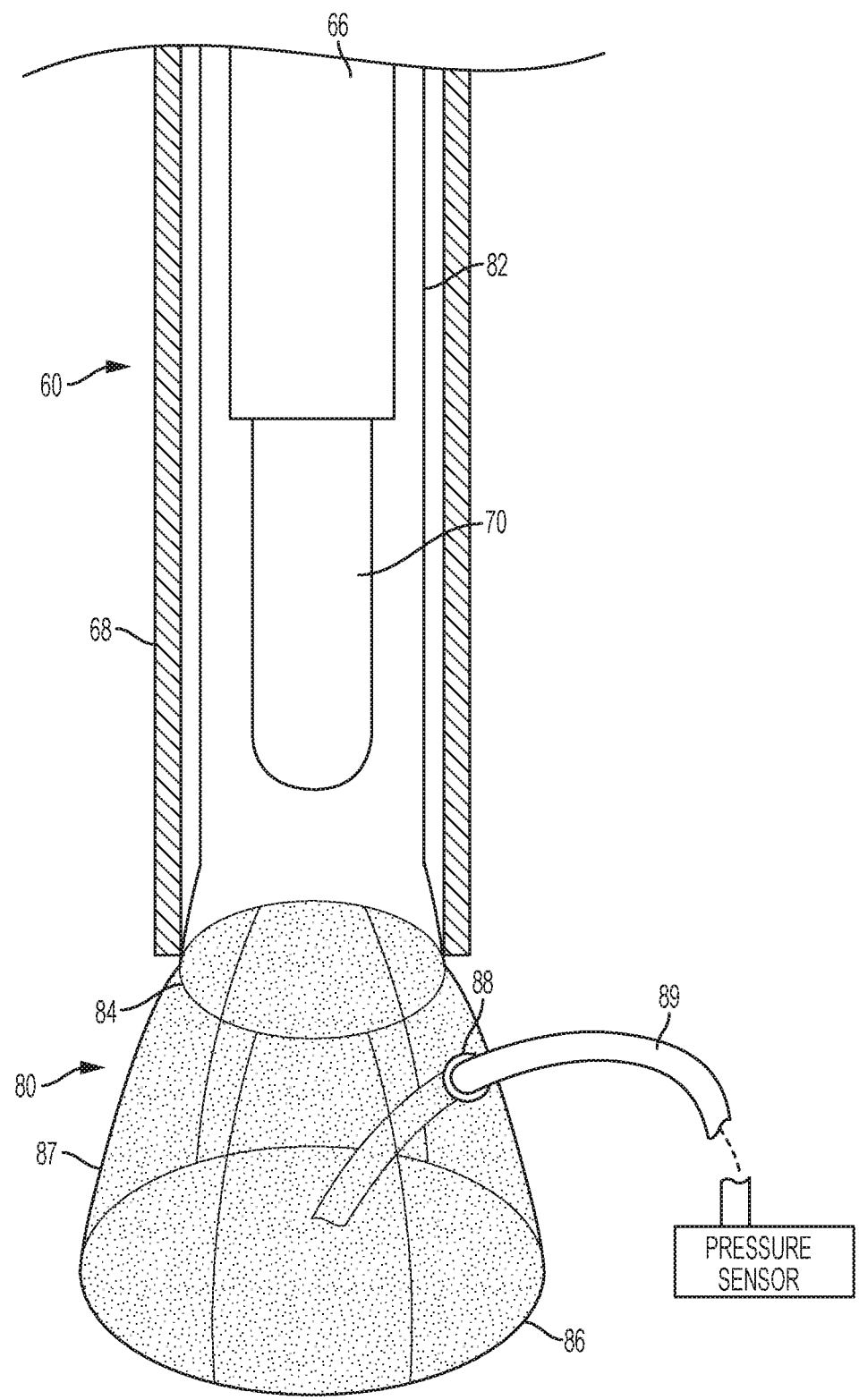
FIG. 2 is a view, partly in cross section and partly perspective, showing a variation of the preferred embodiment of the invention.
Figure 3:
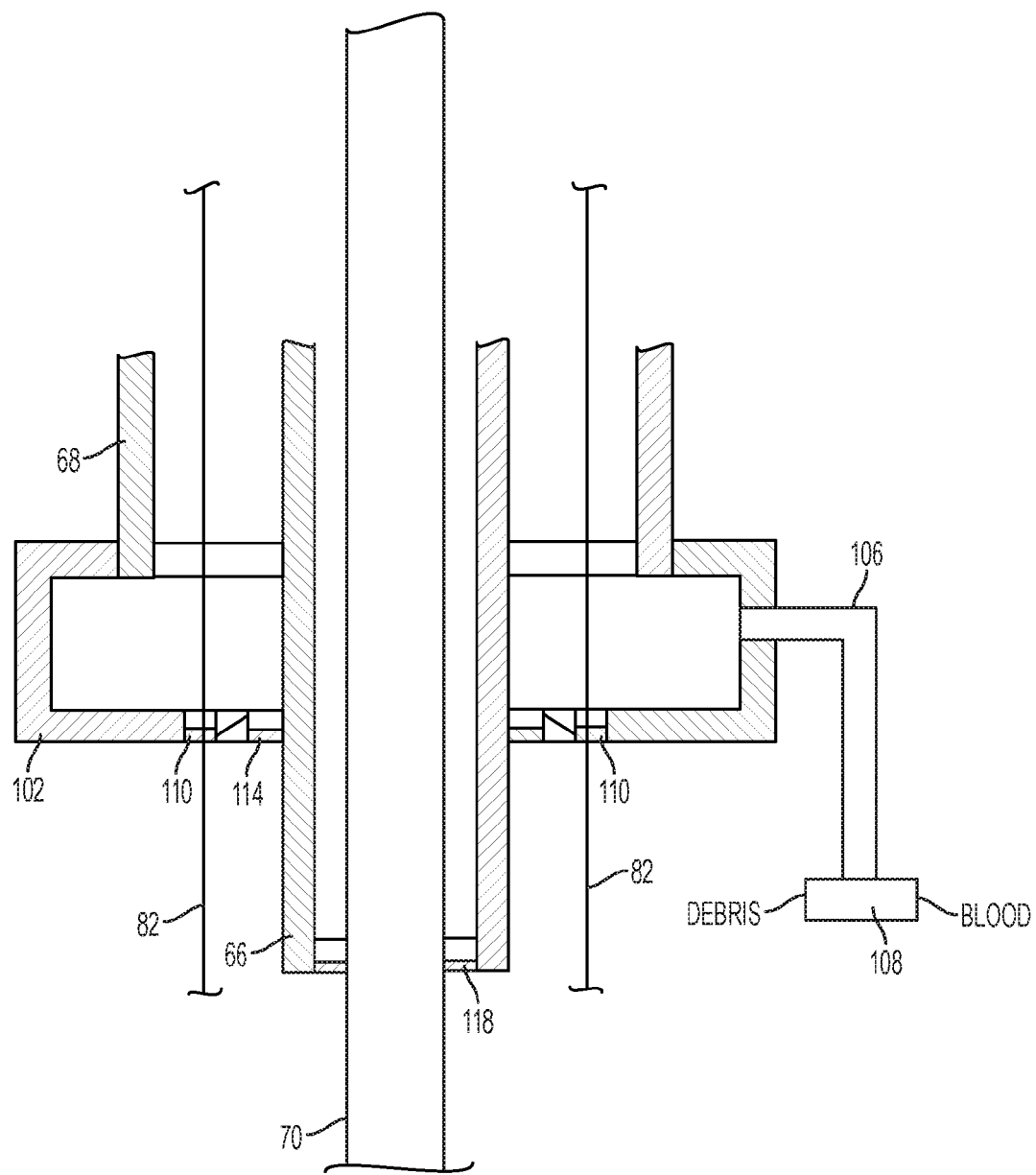
FIG. 3 is a cross-sectional detail view of a housing assembly that forms a component of the preferred embodiment and that will be located outside the patient's body.

Details of the invention are shown in FIGS. 1-3.

The illustrated embodiment is composed essentially of: an assembly 60 (FIG. 2) that includes a guide sheath 68 and a valve implantation system 66 (FIG. 2); a filter 80 and associated control wires 82; and a small diameter tube, or catheter, 89 (FIG. 2). According to this embodiment, components 60 and 80, to be described below, are introduced into the aorta along the same path, for example along the femoral artery via an incision made in the groin and then into the aorta, or through a subclavian artery, as described earlier herein. Catheter 89 (FIG. 2) can be introduced along a different path, for example the radial artery of one arm.

The components shown in FIG. 1 include a guidewire 62 that is introduced first into the ascending aorta, preferably to a point close to the valve that is to be replaced. Then, guidewire 62 is used to introduce an optional first sheath 64, the distal end of which is also brought to a point in the ascending aorta, after which guidewire 62 may be withdrawn, and a sheath 68 is introduced into sheath 64. Sheath 64 is not provided in the embodiment of FIG. 2 and sheath 68 may be brought, while being guided by guidewire 62, to the desired point in the descending aorta.

Sheath 68 houses filter 80, held in a radially compressed state in sheath 68.

Control wires 82 extend through sheath 68 to a proximal location outside of the patient's body. These wires are used to control the desired relative axial movements between filter 80 and sheath 68.

Filter 80 has a generally cylindrical structure with a small diameter end, at the top of the filter in FIG. 2, and a large diameter end, at the bottom of the filter in FIG. 2.

According to a presently preferred embodiment of the invention, the large diameter end of filter 80 is formed to have a generally oval shape with a major diameter of about 40 mm and a minor diameter of the order of 30 mm. This allows the lower end of the filter to better conform to the somewhat oval shape of a normal aorta.

Of course, the dimensions of filter 80 can be varied to conform to aortas having different sizes, for example in children, and shapes.

Filter 80 has a form that may be defined by an outwardly bowed arcuate generatrix of rotation about the longitudinal axis of filter 80 such that the wall of the filter bows outwardly, as shown in FIG. 2.

The framework of the illustrated embodiment is composed of a plurality of wires, or a single wire, including a ring 84 at the small diameter end, a series of longitudinal struts, or ribs, 87, and a circular or oval nitinol ring 86 extending around the large diameter end. Rings 84 and 86 are bonded, or otherwise secured, to the upper and lower ends, respectively, of ribs 87. The sides of filter 80 are covered with a suitable filter fabric having a pore size of, for example, 110 µm.

Filters composed of a framework of wires of memory metal, e.g. nitinol, can be constructed to present a radial expansion/radial compression ratio of 8:1, or more. Therefore, they can be deployed in a sheath or tube having an inner diameter preferably equal to or greater than ⅛ the desired expanded diameter of the large diameter end of the filter.

After sheath 68 has been brought to its desired position in the aorta, close to the defective heart valve, at least approximately where the lower end of filter 80 is to be deployed. Then, sheath 68 can be retracted while filter 80 is held in place by acting on control wires 82. As filter 80 thus exits the lower end of sheath 68, the filter expands, due to the properties of the memory metal wires 84, 86, 87, while it is being deployed to bring it to the desired position and configuration to trap debris.

Then, sheath 68 may be withdrawn from the patient's body or left in place at a distance from the deployed filter.

Filters having a nitinol frame can generally expand radially by a maximum factor of 8 and filter 80 is dimensioned so that in the deployed, or expanded, state, the diameter of the small diameter end can be in the range of 18-26 mm, but can have a smaller diameter if smaller diameter valve implantation systems are developed, and the maximum diameter of the large diameter end can be of the order of 35-40 mm.

After filter 80 has been thus deployed sheath 68 can be brought into the position shown in FIG. 2 to form a seal with ring 84, and a transaortic valve implantation system 66 will be introduced through sheath 68 and then through the small diameter end of filter 80. Typically, introduction of system 66 will be aided by a guidewire such as guidewire 62 shown in FIG. 1, which can be introduced in order to guide system 66 past the defective heart valve.

System 66 encloses an assembly 70 carrying the prosthetic valve to be implanted

The side of filter 80 is provided with an opening defined by a small diameter ring 88, preferably secured to a strut 87. Ring 88 may be made of nitinol wire. Filter fabric is not present in the region enclosed by ring 88, which thus delimits an opening.

Ring 88 is dimensioned to receive a small diameter tube, or catheter, 89, which may have a diameter of the order of 3-7 Fr., preferably 3 Fr., and is preferably dimensioned to achieve a sufficiently close fit with ring 88 to prevent the escape of debris from the region enclosed by filter 80. Tube 89 may be of a type known as a "pigtail" catheter.

Tube 89 will be inserted into ring 88 after filter 80 has been deployed at the desired location. To aid insertion of tube 89, a guidewire (not shown) may be introduced, for example through the right radial artery or the right femoral artery, and then passed through ring 88 into the region enclosed by filter 80. The guidewire may have a diameter of 0.5 Fr. Then, tube 89 is passed over the guidewire and through ring 88, also into the region enclosed by filter 80.

Tube 89 may be employed to inject a contrast fluid that facilitates visualization of the surgery site, such as the aorta and the aortic valve. Such an operation will be further described below. In addition, the distal end of tube 89 can be provided with radiopaque markers to enable its position to be determined fluoroscopically.

Then, system 66 will be operated in a known manner to implant the prosthetic valve.

During implantation of the heart valve, debris will be released and this debris will be confined by filter 80 and can be carried off with blood through sheath 68 to a suction device located outside of the patient's body. This blood and debris can pass through a conventional device, such as a Coulter counter, which detects and counts the debris particles. Suction will be continued until the output of the measuring device indicates that no further debris is present in the blood flow.

After such an indication has been produced, filter 80 can be withdrawn, by acting on the control wires 82, into sheath 68 and all components can then be withdrawn from the patient's body.

Tube 89 may be connected to a suction device outside the patient's body to also suction debris, inevitably accompanied by blood, through tube 89. Outside of the patient's body, debris can be filtered out of the blood and the blood can be returned to the patient's circulatory system, as will be described subsequently herein.

However, according to the present invention, tube 89 is provided at its proximal end, outside the patient's body, with a pressure sensor, and the proximal end of tube 89 is manipulated, or displaced, manually by the physician according to principles known in the medical field to displace the open distal end of tube 89 across the region in front of the existing aortic valve in order to identify the location of the maximum pressure of blood being expelled through the existing aortic valve. This identification of the location may be achieved by fluoroscopically observing one or more radiopaque markers provided at the distal end of tube 89. After this location has been determined, the position of the distal end of tube 89 is used to guide the prosthetic valve of assembly 70 toward the location of maximum blood pressure, thereby enabling the valve to be introduced and implanted at a location that minimizes trauma.

If some lateral displacement of the distal end portion of tube 89 needs to be done, one possibility is to first introduce tube 89 into the aorta, with the pressure sensor removed, and through the opening delimited by ring 88, to provide a bend in a portion of the guidewire that extends from its distal end, and introduce the guidewire into tube 89 so that the end portion is in registry with a corresponding distal portion of tube 89, and manipulate the guidewire, including possibly rotating it, to move the distal portion of tube 89 to the desired location across the aortic valve, all under fluoroscopic observation of a radiopaque marker or markers on the distal end portion of tube 89. Then, the guidewire is removed and the proximal end of tube 89 is connected to the pressure sensor to provide a pressure indication that confirms the position of the distal end of tube 89. Tube 89 may be advanced in and out of the aortic valve, thus entering and exiting the left ventricle. This will give a foolproof method of placing the prosthetic valve implantation device at the desired spot and minimize trauma to the heart.

FIG. 3 is a cross-sectional view showing one possible connection and supporting arrangement for the proximal ends of sheath 68 and system 66 with valve implantation assembly 70 their proximal ends being outside of the patient's body.

This arrangement includes a housing 102 secured to the proximal end of sheath 68 so that the region enclosed by sheath 68 communicates with the region enclosed by housing 102. An outlet conduit 106 extends from the region enclosed by housing 102 to a suction filter device 108 that separates debris from blood and is connected to return the filtered blood to an artery or vein. The debris outlet may be coupled to the above-mentioned suction device.

Housing 102 is provided with a pair of seals 110 through each of which a respective guidewire 82 passes. Housing 102 is also provided with an annular seal 114 through which assembly 66 passes.

Assembly 66, in turn, is provided, at its proximal end, with an annular seal 118 through which device 70 extends.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. Apparatus for carrying out a medical procedure at a site in a patient's blood circulatory system, comprising:
   a first assembly having an outer diameter and including a device to be implanted in the circulatory system;
   a tubular sheath surrounding said first assembly and having a first diameter;
   a hollow tube having a second diameter, distal and proximal ends, and an axial length between said distal and proximal ends, said hollow tube being open at both ends;
   a pressure transducer disposed at said proximal end of said hollow tube for detecting the pressure in said tube; and
   a filter that is collapsible into said sheath and expandable upon being deployed out of said sheath for blocking debris and passing blood in the circulatory system, at the site of the medical procedure, said filter having, when deployed, a radially expanded, generally conical or frustoconical form with a large diameter end, a small diameter end opposite to said large diameter end, and a side surface extending between said large diameter end and said small diameter end,
   said filter:
      comprising a flexible filter material covering said side surface and having pores dimensioned to prevent the passage of debris therethrough while allowing the passage of blood, and having a first opening at said large diameter end, a second opening at said small diameter end, and a third opening in the flexible filter material at said side surface, each said opening having a respective diameter and being free of filter material,
   wherein:
      the diameter of said second opening is substantially equal to the first diameter such that said second opening forms a seal with said sheath when said sheath extends into said filter through said second opening;

said hollow tube is insertable, via said distal end, into said filter through said third opening; and the diameter of said third opening is substantially equal to the second diameter.

2. The apparatus of claim 1, wherein said hollow tube is controllable to displace said distal end in directions transverse to said axial length of said hollow tube.

3. The apparatus of claim 2, wherein said hollow tube is a steerable catheter.

4. The apparatus of claim 1, wherein said first assembly is a transaortic valve implantation assembly and said device to be implanted in the circulatory system is a prosthetic valve.

\* \* \* \* \*